US009119946B2

(12) United States Patent
Dokken et al.

(10) Patent No.: US 9,119,946 B2
(45) Date of Patent: Sep. 1, 2015

(54) ANTISEPTIC APPLICATOR

(71) Applicant: CAREFUSION 2200, INC., San Diego, CA (US)

(72) Inventors: Kenneth M. Dokken, El Paso, TX (US); Jesus G. Flores, El Paso, TX (US); John Gilbert, Lincolnshire, IL (US); James Patrick McDonald, El Paso, TX (US)

(73) Assignee: CAREFUSION 2200, INC., San Diego, CA (US)

( * ) Notice: Subject to any disclaimer, the term of this patent is extended or adjusted under 35 U.S.C. 154(b) by 278 days.

(21) Appl. No.: 13/748,123

(22) Filed: Jan. 23, 2013

(65) Prior Publication Data

US 2014/0205360 A1     Jul. 24, 2014

(51) Int. Cl.
*B43K 5/14*       (2006.01)
*A61F 13/40*     (2006.01)
*A61B 19/00*     (2006.01)
*A61M 35/00*     (2006.01)

(52) U.S. Cl.
CPC .............. *A61M 35/006* (2013.01); *A61B 19/36* (2013.01); *A61M 35/003* (2013.01)

(58) Field of Classification Search
CPC .................................................. A61M 35/006
USPC ........ 401/132–135; 604/3; 15/104.92, 104.93
See application file for complete search history.

(56) References Cited

U.S. PATENT DOCUMENTS

| | | | | |
|---|---|---|---|---|
| 2,696,212 | A * | 12/1954 | Dunmire | 604/195 |
| 4,925,327 | A * | 5/1990 | Wirt | 401/205 |
| 8,425,136 | B2 * | 4/2013 | Littig et al. | 401/133 |
| 8,696,227 | B1 * | 4/2014 | Carter | 401/133 |
| 2007/0231051 | A1 * | 10/2007 | Flores et al. | 401/132 |
| 2008/0292383 | A1 | 11/2008 | Tufts et al. | |
| 2010/0226706 | A1 | 9/2010 | Flores et al. | |
| 2012/0070220 | A1 | 3/2012 | Ruiz, Sr. et al. | |

OTHER PUBLICATIONS

International Search Report and Written Opinion of the International Searching Authority dated May 19, 2014, corresponding to International Application No. PCT/US2014/011650.

* cited by examiner

*Primary Examiner* — Jennifer C Chiang
(74) *Attorney, Agent, or Firm* — Arent Fox LLP

(57) ABSTRACT

An applicator assembly includes a head portion having a proximal end, a distal end, and an interior portion defining a fluid chamber; a container for containing an antiseptic solution coupled to and in fluid communication with the proximal end of the head portion; and an application member in fluid communication with the fluid chamber and comprising a foam, having a first foam layer adjacent a second foam layer, wherein the first foam layer is disposed toward the distal end of the head portion and comprises a dye impregnated therein, and the second foam layer is disposed away from the distal end of the head portion and is free from the dye, and wherein, after the antiseptic solution passes from the container through the fluid chamber, the antiseptic solution passes into the first foam layer, whereupon the dye is solubilized by and tints the antiseptic solution.

19 Claims, 2 Drawing Sheets

ANTISEPTIC APPLICATOR

BACKGROUND

1. Field

The present disclosure relates to an antiseptic applicator and method of use thereof, and more particularly, to an antiseptic applicator that provides a stable tinted antiseptic solution.

2. Description of Related Art

Antiseptic applicators for the preparation of a patient prior to surgery, for example, are known and common in the prior art. Related art applicators rely on various means of actuation to release a self-contained reservoir of antimicrobial solution for sterilization of the patient's skin. For example, a number of applicators are designed with a puncturing means. These applicators typically include a head with a spike, for example, and a sealed container or cartridge. A push or screw motion is employed to axially translate the head toward the sealed container so that the spike may pierce the sealed container and effectuate the release of the solution contained therein. Some examples of applicators using a puncturing means include U.S. Pat. Nos. 4,415,288; 4,498,796; 5,769,552; 6,488,665; and 7,201,525; and U.S. Pat. Pub. No. 2006/0039742, each incorporated by reference.

Other related art applicators rely on breaking an internally situated frangible container or ampoule through the application of a one-way directional force or a localized application of pressure. The directional force is typically applied longitudinally to one end of the ampoule by a pushing motion designed to force the ampoule to break under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,658,084; 5,772,346; 5,791,801; 5,927,884; 6,371,675; and 6,916,133, 7,182,536, each incorporated by reference.

Other related art applicators include other methods of releasing antiseptic solution, such as in U.S. Pat. Pub. No. 2011/0319842, U.S. application Ser. No. 13/328,454, entitled "Antiseptic Applicator," filed Dec. 16, 2011, U.S. application Ser. No. 13/427,371, entitled "Antiseptic Applicator," filed Mar. 22, 2012, and U.S. application Ser. No. 13/458,642, entitled "Antiseptic Applicator," filed Apr. 27, 2012.

Related art applicators often include a pledget provided in a fluid chamber to assist in controlling and/or direct the flow of solution from the solution container to the applicator head. In some related art applicators the pledget may contain a dye. When the solution passes through the pledget, the solution solubilizes the dye and becomes tinted. The solution then passes through the applicator head, to wet a foam, and is applied to a patient's skin. However, using a pledget to store the dye and tint the solution has several disadvantages. The pledget method may not provide consistency of tint intensity. Additionally, there is a possibility of the dye precipitating. With the pledget method, if the precipitation occurs immediately after the solution exits the pledget, clogging will occur in the fluid pathway. An example of an applicator with a pledget includes U.S. Pat. No. 7,182,536.

There remains a need in the field for a novel antiseptic applicator that avoids the complications associated with related art applicators, especially an applicator that will allow for effective tinting of antiseptic solution using mechanisms other than a pledget.

SUMMARY

In accordance with aspects of the present invention, an applicator assembly may include a head portion having a proximal end, a distal end, and an interior portion defining a fluid chamber; a container for containing an antiseptic solution coupled to and in fluid communication with the proximal end of the head portion; and an application member in fluid communication with the fluid chamber and comprising a foam, having a first foam layer adjacent a second foam layer, wherein the first foam layer is disposed toward the distal end of the head portion and comprises a dye impregnated therein, and the second foam layer is disposed away from the distal end of the head portion and is free from the dye, and wherein, after the antiseptic solution passes from the container through the fluid chamber, the antiseptic solution passes into the first foam layer, whereupon the dye is solubilized by and tints the antiseptic solution.

It will become readily apparent to those skilled in the art from the following detailed description, wherein it is shown and described only exemplary configurations of an applicator assembly. As will be realized, the invention includes other and different aspects of an applicator and assembly and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Figure 1:
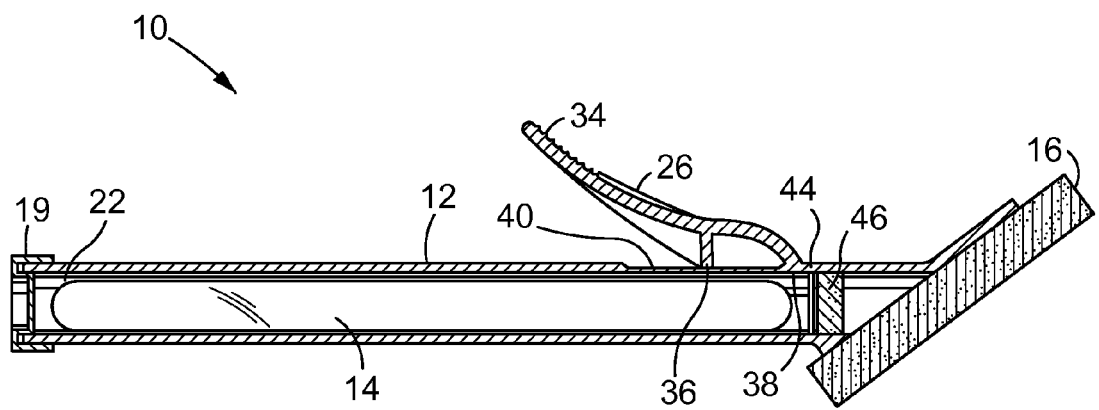
FIG. 1 is a side cutaway view of a related art antiseptic applicator having a pledget.

Various aspects of an antiseptic applicator may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of an antiseptic applicator in addition to the orientation depicted in the drawings. By way of example, if an antiseptic applicator in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of an antiseptic applicator disclosed herein.

FIG. 1 shows an example related art antiseptic applicator 10. Antiseptic applicator 10 generally includes a body 12, and an application member 16 secured to flange of body 12 and a lever 26. A frangible ampoule 14 for containing antiseptic solution is received in body 12. One end is closed with cap 19. Body 12 includes an internal chamber 22. The wall of the applicator includes thinner wall 40. The thickness of the wall of body 12 is reduced around crush area 42. Thin wall 40 makes it easier for crush portion 36 of lever 26 to fracture ampoule 14 when lever 26 is depressed. Pledget 46 is positioned between application member 16 and ampoules 14. Pledget 46 helps control the rate liquid flows from the body and prevents shards of glass from pushing through application member 16 during use of the applicator. Lever 26 includes hinge portion 38, crush portion 36 and handling portion 34 extending from the distal end of lever 26. When the lever 26 is depressed, force is transferred into the crush portion 36 of the lever 26. The pledget 46 is impregnated with a dye so that when antiseptic solution passes through the pledget, the dye is solubilized, thereby tinting the antiseptic solution. The foam application member 16 contains no dye and is comprised of a single uniform piece of foam. In the example related art applicator of FIG. 1, the antiseptic solution is released by actuating the lever 26 with enough force for the ampoule 14 to break. Additional structural and operational description of the applicator 10 may be found in U.S. Pat. No. 7,182,536, which is hereby incorporated by reference herein.

Figure 2:
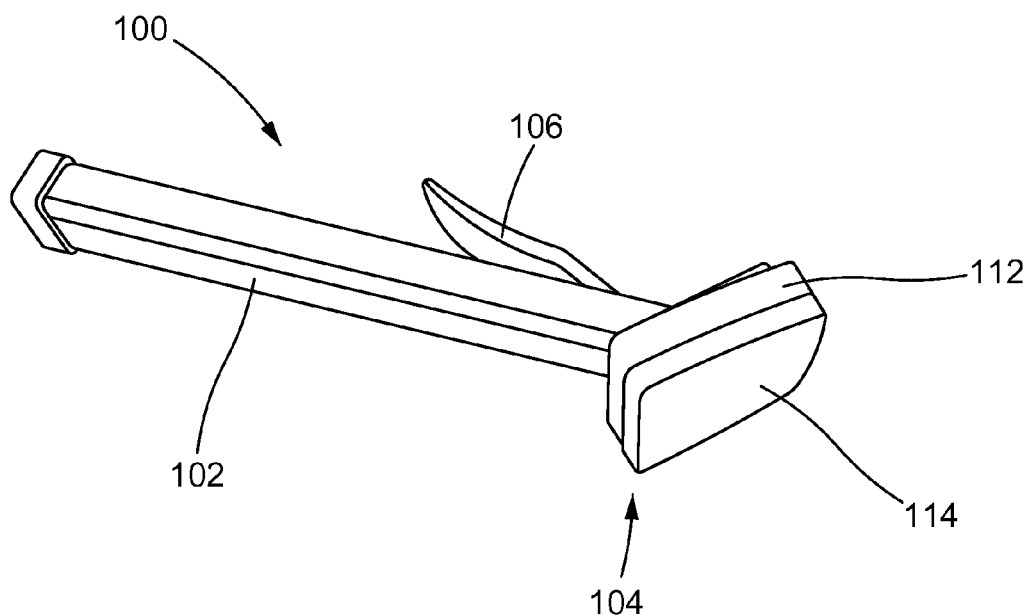
FIG. 2 is a perspective view of an antiseptic applicator in accordance with certain aspects of the present invention.
Figure 3:
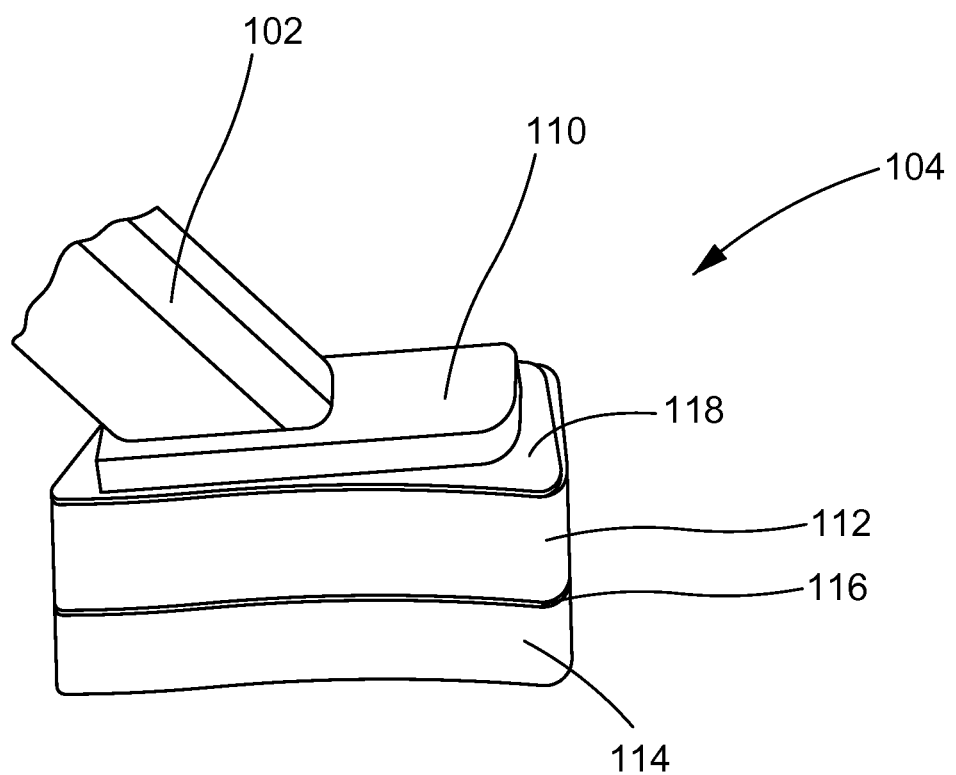
FIG. 3 is a perspective view of the head portion of the antiseptic applicator of FIG. 2.

FIGS. 2 and 3 show an example antiseptic applicator 100 in accordance with aspects of the present invention. As shown in FIGS. 2 and 3, the applicator 100 may comprise a substantially hollow container 102 containing or forming a fluid chamber, a head portion 110 coupled to a distal end of the container 102, and an application member 104 mounted to the head portion 110. The head portion 110 may include a proximal end, a distal end, and an interior portion defining a fluid chamber. As shown in FIG. 3, a proximal end of the head portion 110 may be attached to the distal end of the container 102, while the distal end of the head portion 110 may be attached to the application member 104. Thus, the head portion 110 may be disposed between the container 102 and the application member 104. The applicator 100 may include an actuating arm 106, that, when depressed releases antiseptic solution stored in the container 102. Various example mechanisms and methods for releasing antiseptic solution from the container into the chamber of the head portion are included in the above-listed related art references, each of which is incorporated by reference herein. It should be understood that all of the structure shown in FIG. 2, besides the application member 104, may be substituted with any suitable structure found in the cited related art applicators. That is, one having ordinary skill in the art may apply the application member 104 to any known antiseptic applicator by replacing the application member of the related art antiseptic applicator with the application member 104. For example, the application member 104 may be applied to any of the application members of the above-cited references. A pledget similar to the pledget shown in FIG. 1 may also be included in the antiseptic applicator 100, but may not have dye impregnated therein. Thus, if a pledget is included it may serve the function of flow control, but may not serve the function of tinting the antiseptic solution.

The application member 104 may comprise a foam sponge material, for example, or any suitable material that allows the controlled application of the contained solution from the container 102 to a surface external to the applicator 100. For example, the foam may comprise polyurethane foam. The foam may hydrophilic or hydrophobic, depending on the antiseptic solution contained in the container. Suitable foams or other materials for the application member 104 may be found in the related applicators. In accordance with aspects of the present invention, the application member 104 may be impregnated with a dye. The application member 104 may include a first layer 112 and a second layer 114, wherein the first layer 112 is impregnated with the dye, while the second layer 114 is not impregnated with the dye. The first layer may be impregnated with dye by spray coating, dipping the foam into the dye and allowing it to be adsorbed thereon, or mixing the dye into the foam base as the foam is formed, for example. As shown in FIG. 3, the first foam layer 112 may be positioned or disposed toward the distal end of the head portion 110, and the second foam layer 114 may be disposed away from the distal end of the head portion 110. In other words, the foam layer having the impregnated dye may be the portion of the application member that is attached to the head portion, while the second foam layer without the dye may be the portion that contacts the patient's skin during use. Thus, in this arrangement, during application, the antiseptic solution first passes through the first foam layer having the dye and then passes through the second foam layer without the dye. The foam material chosen may be porous with a particular soak rate, for example, or may be provided with structural features, including slits or apertures, to direct and control the flow rate of the solution through the application member 104. The first and second foam layers may comprise the same or different foam materials. Additionally, the first and second foam layers may be integral with each other. In other words, the application member 104 may be formed from a single piece of foam wherein a first portion of the single foam is impregnated with dye while a second portion is free from the dye. When the first and second foam layers are formed from separate pieces, the layers may be connected by a porous adhesive, sonic lamination, or heat lamination, for example.

The container 102 is preferably a self-contained structure, formed of a suitable material, such as a plastic, e.g., a high-density polyethylene plastic, that is flexible, yet resistant to deformation and chemical leaching. The container 102 may be generally hollow so as to directly contain antiseptic solution or to contain an ampoule, pouch, or the like that stores antiseptic solution. Any of the antiseptic solution releasing mechanisms of the related art applicators that allow the solution to flow from the container 102 into the chamber of the head portion may be implemented in the applicator of the instant invention. This may include devices that puncture an ampoule, tear a pouch, lift a plug, or otherwise provide a fluid pathway for antiseptic solution to flow into the chamber of the head portion. In the variation shown in FIG. 2, the antiseptic solution releasing mechanism includes actuating arm 106, which may be squeezed toward the fluid container 102 to puncture or break an ampoule having antiseptic solution contained therein.

The applicator 100 may further include a filter layer 116 disposed between the first and second foam layers that filters unsolubilized dye. This filter layer prevents unsolubilized dye from passing into the second layer which reduces clogging and provides a more uniformly tinted solution to pass into the second non-dyed foam layer and ultimately to the skin of a patient. The layer between the first and second foam layers may also be utilized to strengthen the connection between the first layer and the second layer. Preferably, the filter layer comprises suitable pore size, pore density, and pore packing, relative to the dye sufficient to prevent unsolubilized dye from passing through the filter. It should be understood that the filter layer can be modified as necessary to possess a compatible pore size, density, and/or pore packing relative to the particular dye. Similarly, raw foam material of the foam layers maybe modified depending on the particular dye. The applicator may also include a wicking layer 118 disposed between the head portion and the first foam layer. The wicking layer allows for better distribution of antiseptic solution into the first foam layer by controlling the flow rate. Wicking layers may be found in the related art applications, such as U.S. Pat. No. 4,925,327, which is incorporated by reference herein.

The dye impregnated within the first foam layer may be anionic or a cationic. The dye may be any dye suitable for medical use, such as dyes approved by the Food and Drug Administration for use in food, drugs, and/or cosmetics (i.e., "D&C" or "FD&C" dyes). For example, the anionic dye may be employed within aqueous antiseptic solutions that include but are not limited to FD&C Blue No. 1 (Brilliant Blue FCF), FD&C Blue No. 2 (Indigo Carmine), FD&C Green No. 3 (Fast Green FCF), FD&C Red No. 3 (Erythrosine), FD&C Red No. 40 (Altura Red), FD&C Yellow No. 5 (Tartrazine), FD&C Yellow No. 6 (Sunset Yellow FCF), D&C Yellow No. 8 (Fluorescein), D&C Orange No. 4, and combinations thereof. Combinations may be implemented to arrive at a particular color. For example, an orange tint may comprise both FD&C Red No. 40 and D&C Yellow No. 8. Examples of cationic dyes include crystal violet, acriflavine, Bismarck brown, malachite green, methyl green, Victoria pure blue BO, azure C, and combinations thereof.

The antiseptic solution may comprise an antiseptic agent and a solvent, preferably an aqueous or an alcoholic solvent. The alcoholic solvent may be any alcohol-based solvent that is suitable for solubilizing antiseptic agent and dye. The solvent should also be suitable for medical use. Example alcoholic solvents include ethanol, isopropanol, n-propanol, and combinations thereof. The alcohol may be present in the solution from about 20 to about 90% v/v. The antiseptic agent may be any antiseptic that is suitable for medical use. The concentration of antiseptic in the antiseptic solution may vary depending on the specific antiseptic agent used, but may generally range from about 0.00001 to 20% w/v. For example, when using octenidine dihydrochloride or an octenidine salt, the preferred concentration may be about 0.0001 to about 0.5% w/v, more preferably about 0.01 to about 0.4% w/v, and more preferably about 0.1 to about 0.3% w/v. For chlorhexidine or a chlorhexidine salt the preferred concentration may be from about 0.5 to about 6.0% w/v, more preferably from about 2.0 to about 4.0% w/v.

The antiseptic agent may include biguanides. Example biguanides include chlorhexidine free base, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine diiodobutyrate, chlorhexidine di-n-valerate, chlorhexidine, dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, chlorhexidine embonate, polyhexamethylene biguanide ("PHMB"), and alexidine (N,N"-Bis(2-ethylhexyl)-3,12-diimino-2,4,11,13-tetraazatetradecanediimidamine; 1,1'hexamethyl-enebis[5-(2-ethylhexyl)biguanide]).

The antiseptic agent may include quaternary ammonium compounds. Example quaternary ammonium compounds include benzalkonium chloride (BZK), benzethonium chloride, other benzalkonium or benzethonium halides, cetylpyridiniumchloride, dequaliniumchloride, N-myristyl-Nmethylmorpholiniummethylsulfate, poly[N-[3-(dimethylammonio)propyl]-N'-[3-(ethyleneoxyethelenedimethylammonio)propyl]urea dichloride], alpha-4-[1-tris(2-hydroxyethyl)ammoniumchloride-2-butenyl]-omegatris(2-hydroxyethyl)ammonium chloride, alpha4-[1-tris(2-hydroxyethyl)ammoniumchloride-2-butenyl]poly[1-dimethylammoniumchloride-2-butenyl]-omegatris(2hydroxyethyl)ammoniumchloride, poly[oxyethylene(dimethyliminio)ethylene(dimethyliminio)-ethylenedichloride], ethylhexadecyldimethylammoniumethylsulfate, dimethylammoniumethylsulfate, dimethylethyl-benzylammoniumchloride, dimethylbenzylammoniumchloride, cetyldimethylethylammoniumbromide, and organosilicon-substituted quaternary ammonium compounds such as 3-(trimethoxysilyl propyloctadecyldimethyl ammonium chloride.

The antiseptic agent may include chlorinated phenol compounds. Example chlorinated phenol compounds may include parachlorometaxylenol, triclosan (2,4,4'-trichloro-2 hydroxy di-phenyl ether), 2-chlorophenol, 3-chlorophenol, 4-chlorophenol, 2,4-dichlorophenol, 2,4,6-trichlorophenol, 2,3,4,6-tetrachlorophenol, pentachlorophenol, 4-chlororesorcinol, 4,6-dichlororesorcinol, 2,4,6-trichlororesorcinol, alkylchlorophenols (including p-alkylo-chlorophenols, o-alkyl-p-chlorophenols, dialkyl-4-chlorophenol, and trialkyl-4-chlorophenol), dichloro-m-xylenol, chlorocresol, o-benzyl-p-chlorophenol, 3,4,6-trichlorophenol, 4-chloro-2-phenylphenol, 6-chloro-2-phenylphenol, o-benzyl-p-chlorophenol, and 2,4-dichloro-3,5-diethylphenol.

Other example antiseptic agents include triclosan, octenidine salts, pyridinium and isoquinolinium compounds, amidine derivatives such as hexamidine isethionate (4,4'-diaminoa,w-diphenoxyhexane isethionate), and bispyridine derivatives such as octenidine(N,WC1,10-decanediyldi-[(4H)-pyridinyl-4-ylidene]-bis(1-octanaminedihydrochloride). Example pyridinium and isoquinolinium compounds include hexadecylpyridinium chloride, cetylpyridinium chloride and alkyl isoquinolinium bromidepyrimidine derivatives such as hexetidine (5-amino-1,3-bis(2-ethylhexyl)-5-methylhexahydropyrimidine).

Preferred examples of antiseptic agents include chlorhexidine salts, octenidine salts, alexidine, halophenols, phenoxyethanol, benzalkonium chloride, parachlorometaxyelanol (PCMX), and combinations thereof.

The antiseptic solution may include a solubilization aid. Example solubilization aids include polyethylene glycol (PEG) average molecular weight 200, PEG average molecular weight 300, PEG average molecular weight 400, and glycerol. The concentration of solubilization aid in an aqueous antiseptic solution may be from about 1 to about 49% v/v.

Additional suitable excipients, antiseptics and dyes that are suitable for use in the instant applicator are provided in WO 04/044068 and WO 09/626,724, each of which is hereby incorporated by reference herein.

Operation of the applicator will now be described. In the pre-use state, the applicator has antiseptic solution stored in the container, either directly contained therein, or via ampoule, pouch, or the like. In the example applicator 100 the antiseptic solution is storied in an ampoule (not shown) within the container 102. Once the user is ready to apply the antiseptic solution to the skin of a patient, for example, at the time of surgery, the operator engages the antiseptic solution releasing mechanism. In the example applicator 100, the operator applies pressure to the actuation arm 106 toward the container 102. Actuation of the antiseptic solution releasing mechanism opens a fluid pathway for the antiseptic solution to travel from the container into the chamber of the head portion 110. In the example applicator 100, actuation of the actuation arm 106 breaks the ampoule containing the antiseptic solution. Once broken, the antiseptic solution is free to flow into the container 102 and then into the chamber of the head portion 110. As noted above, a pledget that is preferably free from dye may be present within the flow path to control the flow into the antiseptic solution into the chamber of the head portion.

From the chamber of the head portion 110, the solution passes into the application member 104. In particular, the solution first passes into the first foam layer 112 of the application member 104, because the first foam layer 112 is connected to the head portion 110. As the antiseptic solution passes through the first foam layer, the solution is preferably distributed throughout the layer and solubilizes dye that is impregnated within the first foam layer. The antiseptic solution becomes tinted as a result of solubilizing the dye. The tinted antiseptic solution then continues to flow into the second layer 114, which does not contain dye. As the tinted solution passes through the second foam layer 114, the tinted antiseptic solution is preferably distributed throughout second foam layer, thus further controlling the flow of antiseptic solution. That is, the second foam layer serves similar flow control and distribution function as the foam in the related art application members. As noted above, the solution may also pass through a wicking layer disposed between the head portion 110 and the first foam layer 112, and/or may pas through a filter layer disposed between the first foam layer 112 and the second foam layer 114.

As the operator applies pressure of the application member 104 to the skin of a patient, the tinted antiseptic solution passes from the second foam layer 114 onto the skin of the patient. Because the solution is tinted, the operator has a visual indication of which portions of the skin are covered with antiseptic solution.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An applicator assembly comprising:
a head portion having a proximal end, a distal end, and an interior portion defining a fluid chamber;
a container for containing an antiseptic solution coupled to and in fluid communication with the proximal end of the head portion; and
an application member in fluid communication with the fluid chamber and comprising a foam, having a first foam layer adjacent a second foam layer,
wherein the first foam layer is disposed toward the distal end of the head portion and comprises a dye impregnated therein, and the second foam layer is disposed away from the distal end of the head portion and is free from the dye, and
wherein, after the antiseptic solution passes from the container through the fluid chamber, the antiseptic solution passes into the first foam layer, whereupon the dye is solubilized by and tints the antiseptic solution.

2. The applicator assembly of claim 1, wherein the first foam layer and the second foam layer and the second foam layer are integral.

3. The applicator assembly of claim 1, wherein a surface of the first foam layer contacts a surface of the second foam layer.

4. The applicator of claim 1, wherein the dye comprises an anionic dye or a cationic dye.

5. The applicator of claim 4, wherein the anionic dye is selected from the group consisting of: Blue No. 1, Blue No. 2, Green No. 3, Red No. 3, Red No. 40, Yellow No. 5, Yellow No. 6, Yellow No. 8, Orange No. 4, and combinations thereof.

6. The applicator of claim 4, wherein the cationic dye is selected from the group consisting of: crystal violet, acriflavine, bismark brown, malachite green, methyl green, Victoria Pure Blue BO, azure C, and combinations thereof.

7. The applicator of claim 1, wherein the antiseptic solution comprises an antiseptic agent and a solvent.

8. The applicator of claim 7, wherein the solvent comprises an alcohol selected from the group consisting of: ethanol, isopropanol, and n-propanol.

9. The applicator of claim 7, wherein the antiseptic agent comprises chlorhexidine or octenidine.

10. The applicator of claim 1, wherein the antiseptic solution comprises a solubilization aid.

11. The applicator of claim 10, wherein the solubilization aid is selected from the group consisting of: polyethylene glycol (PEG) average molecular weight 200, PEG average molecular weight 300, PEG average molecular weight 400, and glycerol.

12. The applicator of claim 11, wherein the concentration of the solubilization aid is about 1% v/v to about 49% v/v.

13. The applicator of claim 1, wherein the first and second foam layers independently comprise polyurethane foam.

14. The applicator of claim 1, wherein the first and second foam layers independently comprise hydrophobic or hydrophilic foam.

15. The applicator of claim 1, further comprising a filter layer disposed between the first and second foam layers that filters unsolubilized dye.

16. The applicator of claim 1, further comprising a wicking layer disposed between the head portion and the first foam layer.

17. The applicator of claim 1, wherein the container contains antiseptic solution.

18. The applicator of claim 1, further comprising an antiseptic solution releasing mechanism that releases the antiseptic solution from the container upon actuation.

19. The applicator of claim 1, wherein the first foam layer and the second foam layer comprise the same foam material.

* * * * *